United States Patent
Lo

(12) 
(10) Patent No.: US 6,497,679 B2
(45) Date of Patent: Dec. 24, 2002

(54) SAFETY HYPODERMIC SYRINGE HAVING A DESIGN FOR EASY POSITIONING OF THE NEEDLE CANNULA HOLDER

(75) Inventor: Pi-Chang Lo, Taipei (TW)

(73) Assignee: M.K. Meditech Co., Ltd., Taoyuan Hsien (TW)

( * ) Notice: Subject to any disclaimer, the term of this patent is extended or adjusted under 35 U.S.C. 154(b) by 156 days.

(21) Appl. No.: 09/754,329

(22) Filed: Jan. 5, 2001

(65) Prior Publication Data

US 2002/0055719 A1 May 9, 2002

(30) Foreign Application Priority Data

Nov. 8, 2000 (TW) ........................................ 89123640 A

(51) Int. Cl.⁷ ............................................... A61M 5/00
(52) U.S. Cl. ...................... 604/110; 604/195; 604/197
(58) Field of Search ................................ 604/110, 162, 604/164.08, 165.01, 165.02, 192, 195, 196, 197, 198

(56) References Cited

U.S. PATENT DOCUMENTS

| | | | | |
|---|---|---|---|---|
| 4,995,874 A | * | 2/1991 | Strickland | 604/110 |
| 5,395,337 A | * | 3/1995 | Clemens et al. | 604/110 |
| 5,531,705 A | * | 7/1996 | Alter et al. | 604/110 |
| 5,785,687 A | * | 7/1998 | Saito | 604/110 |
| 5,788,672 A | * | 8/1998 | Saito | 604/110 |

\* cited by examiner

*Primary Examiner*—Lesley D. Morris
*Assistant Examiner*—John Fristoe
(74) *Attorney, Agent, or Firm*—Bacon & Thomas, PLLC

(57) ABSTRACT

A safety hypodermic syringe is disclosed including a barrel and a needle cannula holder. The barrel comprises a stop ring suspended inside the front section thereof, and connecting ribs connected between the inside wall thereof and the stop ring. The needle cannula holder fastened to the front section of the barrel comprises a front extension hub holding a needle cannula, a plurality of wedge-like locating blocks protruded from the periphery of the front extension hub and stopped at the front side of the stop ring, and a shoulder stopped at the rear side of the stop ring. The needle cannula holder is constrained by an axial force exerted from the stop ring and connecting ribs of the barrel. After the service of the safety hypodermic syringe, the needle cannula holder is pushed more forwards to force the shoulder against the connecting ribs and to break the connecting ribs separate, for enabling the needle cannula holder and the needle cannula to be further pulled backwards into the inside of the barrel.

8 Claims, 3 Drawing Sheets

SAFETY HYPODERMIC SYRINGE HAVING A DESIGN FOR EASY POSITIONING OF THE NEEDLE CANNULA HOLDER

BACKGROUND OF THE INVENTION

1. Field of the Invention

The present invention relates to a safety hypodermis syringe and, more particularly, to such a safety hypodermic syringe, which enables the needle cannula holder to be easily installed.

2. Description of Related Art

In a regular safety hypodermic syringe, the plunger has a hook at the front side, which is forced into engagement with the needle cannula holder after the service of the safety hypodermic syringe, enabling the needle cannula holder and the needle cannula to be pulled backwards with the plunger and received inside the barrel. According to conventional designs, the needle cannula holder is press-fitted into the inside of the front section of the barrel. The outer diameter of the needle cannula holder and the inner diameter of the front section of the barrel must match perfectly using the radial constraint force, so that the needle cannula holder can be positively positioned in the front section of the barrel. When inserting the needle cannula holder into the front section of the barrel, much force should be applied to the needle cannula holder, and the parts of the safety hypodermic syringe tend to be damaged when forcing the needle cannula holder into the front section of the barrel.

According to conventional safety hypodermic syringe fabrication methods, the needle cannula holder and the barrel are respectively molded from plastics by a respective multi-cavity injection-mold. Because the injection environment (location of running gate, injection temperature, cooling speed, and etc.) of each cavity in a multi-cavity injection-mold differs, it is difficult to control the precision size of every finished needle cannula holder and barrel. Because dimensional tolerance is inevitably, it is difficult to achieve perfect matching between the inner diameter of the barrel and the outer diameter of the needle cannula holder. Loose fitness between the outer diameter of the needle cannula holder and the inner diameter of the barrel may cause the needle cannula holder easily loosened from the barrel. Excessively tight fitness between the outer diameter of the needle cannula holder and the inner diameter of the barrel may cause the needle cannula holder unable to be pulled backwards with the plunger.

Therefore, it is desirable to provide an improved hypodermic syringe to mitigate and/or obviate the aforementioned problems.

SUMMARY OF THE INVENTION

The main object of the present invention is to provide a safety hypodermic syringe, which uses axial constraint force, instead of radial constraint force, to hold the needle cannula holder firmly in the barrel. It is another object of the present invention to increase the productivity of a safety hypodermic syringe. It is still another object of the present invention to provide a safety hypodermic syringe, which enables the needle cannula holder and the needle cannula to be easily pulled backwards and received inside the barrel after the service of the safety hypodermic syringe.

To achieve the objects, the safety hypodermic syringe of the present invention comprises a barrel and a needle cannula holder fastened to the barrel and holding a needle cannula. The barrel has a stop device suspended inside the front section of the barrel, and at lease two connecting ribs connected between the inside wall of the barrel and the stop device. The needle cannula holder comprises a front extension hub holding a needle cannula, a plurality of locating blocks protruded from the periphery of the front extension hub and stopped at the front side of the stop device, and a shoulder stopped at the rear side of the stop device. Therefore, the needle cannula holder is constrained by an axial force exerted from the stop device and connecting ribs of the barrel. After the service of the safety hypodermic syringe, the needle cannula holder is pushed more forwards to force the shoulder against the connecting ribs and to break the connecting ribs separate, for enabling the needle cannula holder and the needle cannula to be further pulled backwards into the inside of the barrel.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
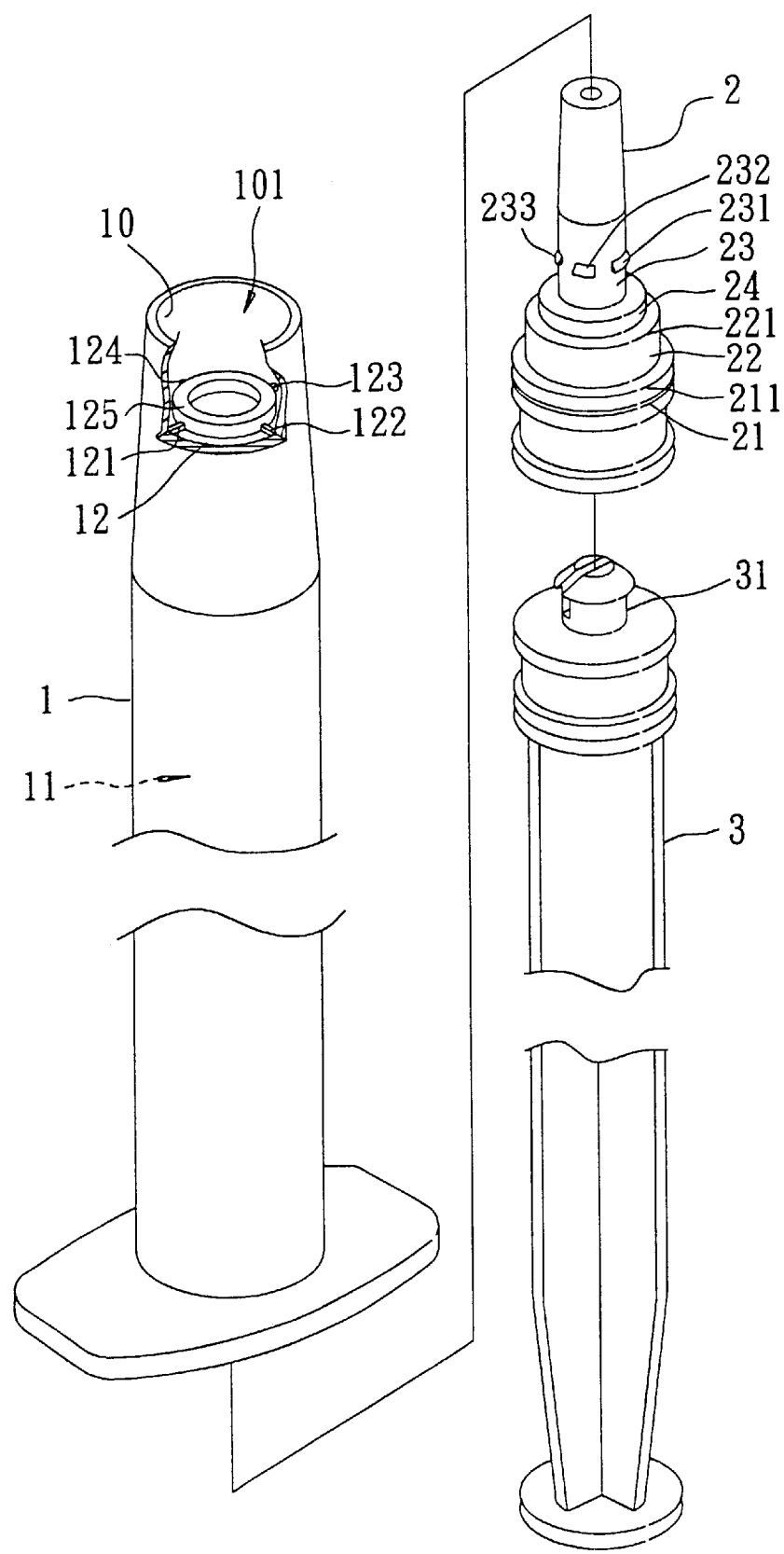
FIG. 1 is an exploded view of a safety hypodermic syringe according to the preferred embodiment of the present invention.
Figure 2:
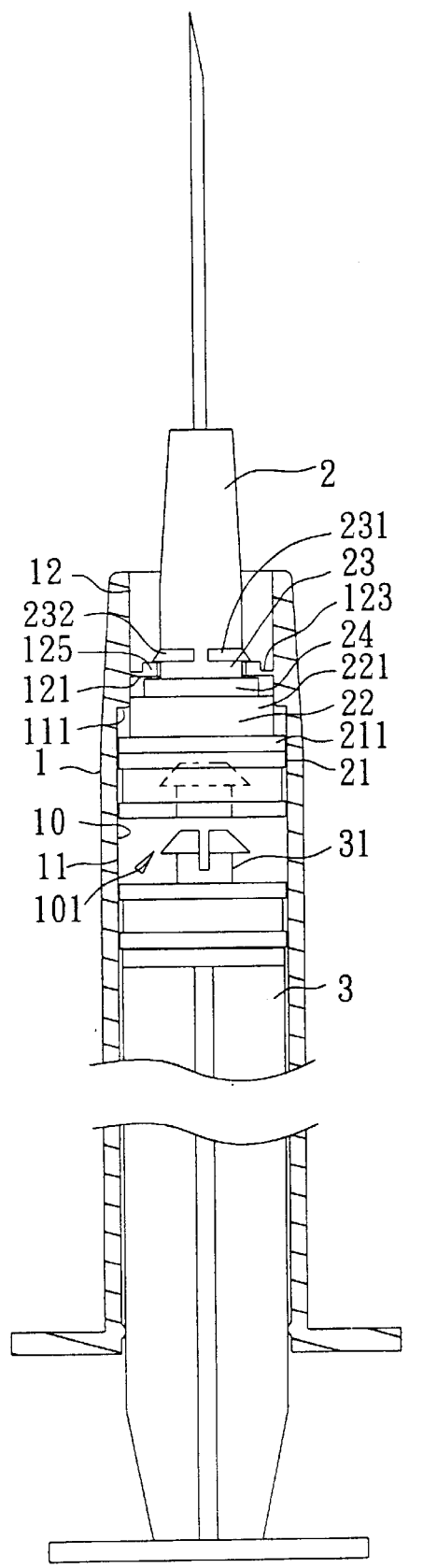
FIG. 2 is a sectional view of the safety hypodermic syringe according to the preferred embodiment of the present invention.

With reference to FIGS. 1 and 2, there is shown a safety hypodermic syringe comprised of a barrel 1, a needle cannula holder 2, and a plunger 3. The barrel 1 comprises an inside wall 10 defining a receiving chamber 101. The inside wall 10 comprises a rear section 11 of relatively greater diameter, a front section 12 of relatively smaller diameter, a step 111 connected between the rear section 11 and the front section 12, a stop ring 125 suspended within the front section 12, and four connecting ribs 121,122,123 and 124 equiangularly spaced around and radially connected between the front section 12 and the stop ring 125. The stop ring may alternatively separate into several segments as of a plurality of stoppers. The connecting ribs may arrange unequiangularly in another embodiment.

The needle cannula holder 2 comprises a front extension hub 23 adapted to hold a needle cannula, a rear section 21 fitting the inner diameter of the rear section 11 of the barrel 1, a front section 22 axially connected between the rear section 21 and the front extension hub 23 and fitting the inner diameter of the front section 12 of the barrel 1, a step 211 formed between the front section 22 and the rear section 21, a bearing portion 24 formed between the front extension hub 23 and the front section 22, a shoulder 221 formed between the bearing portion 24 and the front section 22, and a plurality of wedge-like locating blocks 231, 232, 233 . . . (or in arc-like cross section) protruded from the periphery of the front extension hub 23. The locating blocks may alternatively connect together to form an outside ring protruded from the periphery of the front extension hub.

During assembly of the safety hypodermic syringe, the needle cannula holder 2 is inserted into the receiving chamber 101 of the barrel 1 from the rear side. Because the locating blocks 231, 232, 233 . . . have a wedge-like cross section, the locating blocks 231, 232, 233 . . . can easily be inserted through the stop ring 125 and then stopped at the front side of the stop ring 125. As illustrated in FIG. 2, the thickness of the stop ring 125 is just disposed between the locating blocks 231, 232, 233 . . . and the bearing portion 24, therefore the needle cannula holder 2 is constrained by the stop ring 125 with an axial force exerted from the locating blocks 231,232,233 . . . and the bering portion 24. Further, because the locating blocks 231, 232, 233 . . . are stopped at the front side of the stop ring 125, the needle cannula holder 2 overcome backward force during injection of the safety hypodermic syringe. Therefore, the needle cannula holder 2 can easily positively be positioned in the front part of the receiving chamber 101 of the barrel 1.

As indicated above, the invention eliminates the possibility of causing damage due to the press-fitting operation of the needle cannula holder into the barrel according to the prior art. The precision requirements of the inner diameter of the barrel and the outer diameter of the needle cannula holder are less critical according to the present invention. The fabrication of the parts of the safety hypodermic syringe of the present invention is simple and inexpensive, which increases the productivity.

Figure 3:
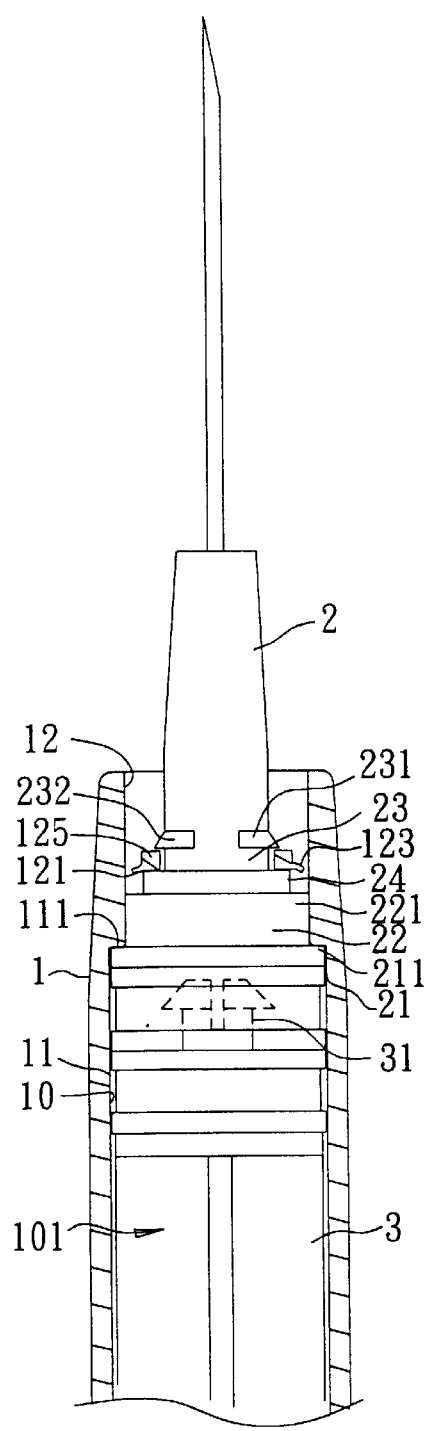
FIG. 3 is a schematic drawing showing a breaking action of the preferred embodiment of the present invention.

Referring to FIG. 3, after injection, the plunger 3 is pushed to move the needle cannula holder 2 more forwards, and to force the step 211 of the needle cannula holder 2 stop at the step 111 of the barrel 1 and the shoulder 221 against the connecting ribs 121, 122, 123 and 124, thereby causing the connecting ribs 121, 122, 123 and 124 to be broken. After the connecting ribs 121, 122, 123 and 124 had been broken, the stop ring 125 is separated from the barrel 1, enabling the needle cannula holder 2 can be moved axially free in the barrel 1. Therefore, when pulling the plunger 3 backwards, the needle cannula holder 2 is moved with the front split bolt 31 of the plunger 3 and received inside the barrel 1.

Figure 4:
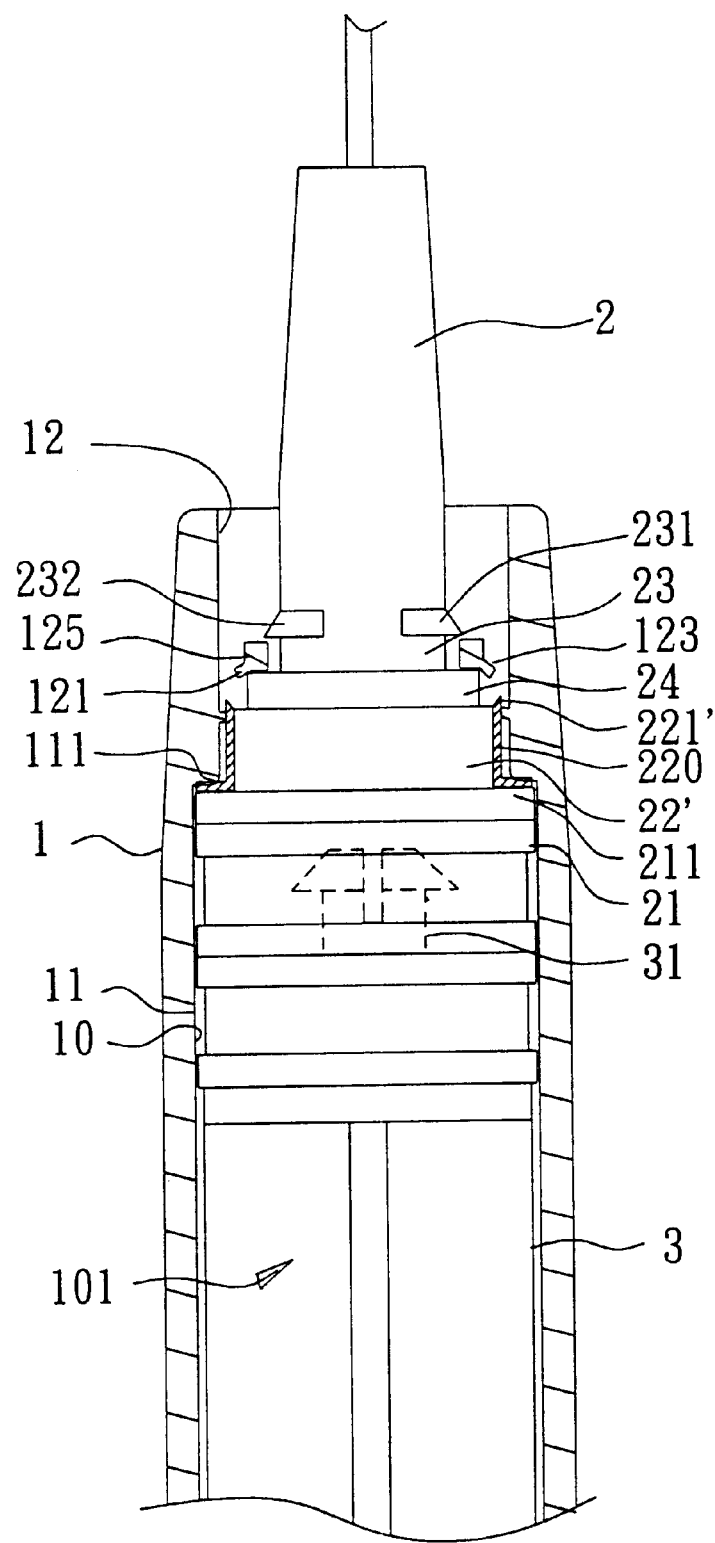
FIG. 4 illustrates an alternate embodiment of the present invention.

FIG. 4 shows an alternate embodiment of the present invention. According to this alternate form, the diameter of the front section 22' of the needle cannula holder 2 is relatively smaller than the aforesaid first embodiment of the present invention, and a bush 220 of hard material is sleeved onto the periphery of the front section 22' and fitted inside the front section 12 of the barrel 1 to reinforce the strength of the shoulder 221' so that the shoulder 221' can break the connecting ribs 121, 122, 123 and 124 easier when pushed forwards. The bush 220 can be made of stainless steel, any other metal bush, or hard plastics such as engineering plastic.

Although the present invention has been explained in relation to its preferred embodiments, it is to be understood that many other possible modifications and variations can be made without departing from the spirit and scope of the invention as hereinafter claimed.

What is claimed is:
1. A safety hypodermic syringe comprising:
   a barrel, said barrel comprising an inside wall defining a receiving chamber, said inside wall comprising a rear section, a front section of diameter relatively smaller than the rear section of said barrel, a step connected between the rear section and front section of the inside wall of said barrel, a stop means suspended within the front section of the inside wall of said barrel, and at least two connecting ribs radially connected between the front section of the inside wall of said barrel and said stop means; and
   a needle cannula holder, said needle cannula comprising a front extension hub inserted through said stop means of said barrel and holding a needle cannula, a rear section fitting the inner diameter of the rear section of the inside wall of said barrel, a front section axially connected between the rear section of said needle cannula holder and said front extension hub and fitting the inner diameter of the front section of the inside wall of said barrel, a step formed between the front section and the rear section of said needle cannula holder and adapted for stopping at the step of said barrel, a shoulder formed between said front extension hub and the front section of said needle cannula holder and stopped at a rear side of said stop means of said barrel, and locating means protruded from the periphery of said front extension hub and stopped at a front side of said stop means of said barrel;
   when said needle cannula holder is pushed forwards after the service of the safety hypodermic syringe, said shoulder is forced against said connecting ribs to break said connecting ribs and to separate said stop means from the inside wall of said barrel, for enabling said needle cannula holder and said needle cannula to be further pulled backwards into the inside of said barrel.

2. The safety hypodermic syringes as claimed in claim 1, wherein said stop means of said barrel is a stop ring.

3. The safety hypodermic syringe as claimed in claim 1, wherein said needle cannula holder further comprises a bearing portion formed between said front extension hub and said shoulder and adapted to bear said stop means.

4. The safety hypodermic syringe as claimed in claim 1, wherein said needle cannula holder further comprises a hard bush sleeved onto the front section of said needle cannula holder and fitted inside the front section of the inside wall of said barrel.

5. The safety hypodermic syringe as claimed in claim 4, wherein said hard bush is a metal bush.

6. The safety hypodermic syringe as claimed in claim 1, wherein said locating means comprises a plurality of locating blocks equiangularly spaced around the periphery of said front extension hub.

7. The safety hypodermic syringe as claimed in claim 1, wherein said locating means having a wedge-like cross section.

8. The safety hypodermic syringe as claimed in claim 1 further comprising a plunger inserted into the receiving chamber of said barrel.

* * * * *